US009586045B2

(12) United States Patent
Behar-Cohen et al.

(10) Patent No.: US 9,586,045 B2
(45) Date of Patent: Mar. 7, 2017

(54) METHODS AND PHARMACEUTICAL COMPOSITIONS FOR THE TREATMENT OF AN OCULAR DISEASE IN A SUBJECT

(75) Inventors: Francine Behar-Cohen, Paris (FR); Elodie Touchard, Paris (FR); Marianne Berdugo Polak, Paris (FR)

(73) Assignee: Institut Nationale de la Santé et de la Recherche Médicale, Paris (FR)

( * ) Notice: Subject to any disclaimer, the term of this patent is extended or adjusted under 35 U.S.C. 154(b) by 22 days.

(21) Appl. No.: 14/238,607

(22) PCT Filed: Aug. 14, 2012

(86) PCT No.: PCT/IB2012/054139
§ 371 (c)(1),
(2), (4) Date: May 22, 2014

(87) PCT Pub. No.: WO2013/024433
PCT Pub. Date: Feb. 21, 2013

(65) Prior Publication Data
US 2014/0309613 A1    Oct. 16, 2014

(30) Foreign Application Priority Data

Aug. 16, 2011 (EP) .................................... 11306046

(51) Int. Cl.
| | | |
|---|---|---|
| *C12N 13/00* | (2006.01) | |
| *A61K 48/00* | (2006.01) | |
| *A61N 1/32* | (2006.01) | |
| *A61K 38/18* | (2006.01) | |
| *A61K 9/00* | (2006.01) | |

(52) U.S. Cl.
CPC ............ *A61N 1/327* (2013.01); *A61K 9/0048* (2013.01); *A61K 38/1866* (2013.01); *A61K 48/0075* (2013.01); *A61K 48/0083* (2013.01)

(58) Field of Classification Search
None
See application file for complete search history.

(56) References Cited

U.S. PATENT DOCUMENTS 7,947,267 B2 * 5/2011 Francois et al. ............. 424/93.1
2008/0183123 A1 * 7/2008 Behar-Cohen et al. ........ 604/21

FOREIGN PATENT DOCUMENTS

| WO | 02/083184 A2 | 10/2002 |
|---|---|---|
| WO | 2007/106381 A2 | 9/2007 |
| WO | 2010/019786 A1 | 2/2010 |

OTHER PUBLICATIONS

Kachi, "Nonviral ocular gene transfer" Gene Therapy, Jan. 1, 2005, pp. 843-851, vol. 12, MacMillan Press Ltd., Basingstoke, GB.
Peden et al., "Ab-Externo AAV-Mediated Gene Delivery to the Suprachoroidal Space Using a 250 Micron Flexible Microcatheter", PLOS ONE, Jan. 1, 2011, p. e17140, vol. 6, No. 2.
Olsen et al., "Cannulation of the Suprachoroidal Space: A Novel Drug Delivery Methodology to the Posterior Segment", American Journal of Ophthalmology, Nov. 1, 2006, pp. 777-787, vol. 142, No. 5, Ophthalmic Publ., Chicago, IL.
Andrieu-Soler et al, "Ocular gene therapy: a review of nonviral strategies", Molecular Vision, Jan. 1, 2006, pp. 1334-1347, vol. 12, Atlanta, GA.
Kowalczuk et al., "Local ocular immunomodulation resulting from electrotransfer of plasmid encoding soluble TNF receptors in the ciliary muscle", Investigative Ophthalmology & Visual Science, Apr. 1, 2009, pp. 1761-1768, vol. 50, No. 4, Association for Research in Vision and Ophthalmology, US.
Matsuda et al., "Electroporation and RNA interference in the rodent retina in vivo and in vitro", Proceedings of the National Academy of Sciences of USA, Jan. 6, 2004, pp. 16-22, vol. 101, No. 1, National Academy of Science, Washington, DC.
Asahara et al., "Induction of gene into the rabbit eye by iontophoresis: preliminary report" Japanese Journal of Ophthalmology, Jan. 1, 2001, pp. 31-39, vol. 45, No. 1, Maruzen Co., Ltd., Tokyo, JP.
Samirkumar et al., "Suprachoroidal Drug Delivery to the Back of the Eye Using Hollow Microneedles", Pharmaceutical Research, Sep. 21, 2010, pp. 166-176, vol. 28, No. 1, Kluwer Academic Publishers-Plenum Publishers, NL.

* cited by examiner

*Primary Examiner* — Janice Li
(74) *Attorney, Agent, or Firm* — Whitham, Curtis & Cook, P.C.

(57) ABSTRACT

Provided herein is a method for treating an ocular disease in a subject comprising the steps consisting of i) delivering a pharmaceutical composition formulated with a therapeutic nucleic acid of interest into the suprachoroidal space of the diseased eye and ii) exposing the region where the pharmaceutical composition was delivered to an electrical field.

20 Claims, No Drawings

METHODS AND PHARMACEUTICAL COMPOSITIONS FOR THE TREATMENT OF AN OCULAR DISEASE IN A SUBJECT

CROSS-REFERENCE TO RELATED APPLICATIONS

This application is a 371 of international application No. PCT/IB2012/054139 filed Aug. 14, 2012 which claims benefit to European application No. 11306046.1 filed Aug. 16, 2011, both of which are incorporated herein by reference.

FIELD OF THE INVENTION

The present invention relates to methods and pharmaceutical compositions for the treatment of an ocular disease in a subject.

BACKGROUND OF THE INVENTION

In recent years, there have been exciting new advances for the treatment of ocular diseases such as age-related macular degeneration and diabetic retinopathy, using biotherapies. Because the eye is a small, confined organ, isolated by barriers, it has been identified as an organ of choice for local gene therapy.

For example, hereditary retinal dystrophies are due to mutations in gene encoding proteins in photoreceptors (cones and rods) or in retinal pigment epithelial cells (RPE). Whilst gene replacement in photoreceptor cells is still under pre-clinical evaluation, the most striking advances in this field have been made for RPE65 gene replacement in RPE cells, for the treatment of Leber congenital amaurosis (LCA). Not only was it shown that viral gene transfer in the RPE was feasible and efficient in animal models, but recently, patients have received the sub retinal injection of rAAV4 with promising functional results, providing hope for patients suffering from blinding diseases.

Viral vectors allow efficient transfection of RPE cells and have served to validate proof of concepts, but the long-term persistence of viral particles into the retina and the brain continues to raise safety concerns, particularly when treatment is being applied in young children.

When injected into the vitreous, viral vectors do not reach the RPE cells and only their sub-retinal injection have been shown effective for targeting RPE cells or photoreceptors. Moreover, using the sub retinal injection, RPE cells are only transfected in, and in the vicinity of the detached retina area, which implies detaching the macula when central vision recovery is targeted. Such a macular detachment may be associated with vision threatening. Indeed, it is well known that poor vision recovery after retinal detachment is correlated with macular detachment. Recent work using spectral domain OCT has provided evidence that following successful surgical treatment of retinal detachment, 62% of the eyes presented anatomical foveal abnormalities and that particularly, external limiting membrane disruption, observed only when the macula was detached before surgery, was associated with the worst vision prognosis. Even if controversies still exist regarding the factors that may predict vision recovery after macular detachment, the health of the macula at the time of reattachment is probably the most critical variable. In diseased eyes, knowing the uncertainty of central vision recovery after macular detachment, it is difficult to ensure that submacular injection is not risky.

Many non-viral gene transfer vectors or methods have been developed and adapted for ocular gene therapy (Andrieu-Soler C Mol Vis 2006 12:1334; Bejjani R A Sury Ophthalmol 2007 52:196; Bloquel C Adv Drug Deliv Rev 2006 58:1224). Among those, electroporation, also called "electrotansfer" where the current drives plasmid DNA into cells, is among the most efficient ((Mir L M Adv Genet 2005 54:83; Mir L M Methods Mol Biol 2008 423:3; Isaka Y Expert Opin Drug Deliv 2007 4:561) and has been developed up to clinical evaluation (Daud A I J Clin Oncol 2008 26:5896). Previous reports have shown that after sub retinal administration of the plasmids, electroporation allowed the efficient tranfection of new-born murine RPE (Matsuda T Proc Natl Acad Sci USA 2004 101:16) and delayed retinal degeneration in animal models (Chen B Science 2009 323: 256). Efficient and prolonged RPE transfection was also achieved in the adult rat using a combination of sub retinal plasmids injection containing specific RPE promoter and electroporation (Kachi S Gene Ther 2005 12:843; Johnson C J Mol Vis 2008 14:2211).

The suprachoroidal space is a potential space in the eye that is located between the choroid, which is the inner vascular tunic, and the sclera, the outer layer of the eye. The suprachoroidal space extends from the anterior portion of the eye posterior to the ciliary body to the posterior portion of the eye up to the optic nerve. The suprachoroidal space of the eye has been thus studied as a possible route for drug delivery. See, e.g., Olsen, et al., American J. Opthamology 142(5): 777-87 (November 2006); PCT Patent Application Publication No. WO 2007/100745 to Iscience Interventional Corporation. The suprachoroidal space may indeed provide a potential route of access from the anterior region of the eye to treat the posterior region. However said route has not been envisaged for non-viral gene therapy.

SUMMARY OF THE INVENTION

The present invention relates to a method for treating an ocular disease in a subject comprising the steps consisting of i) delivering a pharmaceutical composition formulated with a therapeutic nucleic acid of interest into the suprachoroidal space of the diseased eye and ii) exposing the region where the pharmaceutical composition was delivered to an electrical field.

DETAILED DESCRIPTION OF THE INVENTION

The inventors have evaluated whether the suprachoroidal injection of a plasmid solution in the rat eye, associated with extra ocular electroporation could be efficient for the transfection of the choroid and the RPE cells and/or the neuroretina. They bring here the proof of concept that using this minimally invasive technique, that does not require sub retinal injection and subsequent detachment, not only RPE cells and choroidal cells, but also photoreceptors are efficiently transfected. The invention thus relates to the use of such a method for the treatment of an ocular disease in a subject.

Accordingly, the present invention relates to a method for treating an ocular disease in a subject comprising the steps consisting of i) delivering a pharmaceutical composition formulated with a therapeutic nucleic acid of interest into the suprachoroidal space of the diseased eye and ii) exposing the region where the pharmaceutical composition was delivered to an electrical field.

The nucleic acid to be used in the instant invention can be any nucleic acid of interest exhibiting a biological property. More particularly, the nucleic acid can be any nucleic acid encoding a natural, truncated, artificial, chimeric or recombinant product [e.g., a polypeptide of interest (including a protein or a peptide), a RNA, etc.] exhibiting a biological activity.

The nucleic acid is preferably a desoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). The nucleic acid may be single stranded or multistranded nucleic acid, preferably double-stranded nucleic acid or may be complexed. The nucleic acid may comprise hybrid sequences or synthetic or semi-synthetic sequences. It may be obtained by any technique known to persons skilled in the art, and especially by screening libraries, by chemical synthesis, or alternatively by mixed methods including chemical or enzymatic modification of sequences obtained by screening libraries.

In a particular embodiment, the therapeutic nucleic acid is of synthetic or biosynthetic origin, or extracted from a virus or from a unicellular or pericellular eukaryotic or prokaryotic organism.

The therapeutic nucleic acid used in the present invention may be naked, may be complexed with any chemical, biochemical or biological agent, may be inserted in a vector, etc., when administered to the suprachoroidal space.

As used herein, the term "naked DNA" refers to any nucleic acid molecule which is not combined with a synthetic, biosynthetic, chemical, biochemical or biological agent improving the delivery or transfer of said DNA, or facilitating its entry into the cell.

As used herein, the term "vector" refers to a nucleic acid molecule capable of transporting another nucleic acid to which it has been linked. This term also refers in the present application to any delivery carrier, such as a composition associated to a therapeutic or prophylactic nucleic acid in order to increase its cellular delivery.

Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form, are not bound to the chromosome. In the present invention, the plasmid is the most commonly used form of vector. The plasmid is a preferred form of naked DNA according to the invention.

Vectors may also be episomal DNA, yeast artificial chromosomes, minichromosomes or viral vectors wherein the viral vector is selected from the group consisting of a lentivirus, an adenovirus, an adeno-associated virus and a virus-like vector.

The vector may also be a lipid vesicle such as a liposome. Lipid based compounds which are not liposomes may further be used. For example, lipofectins and cytofectins are lipid-based positive ions that bind to negatively charged nucleic acid and form a complex that can ferry the DNA across a cell membrane. The invention is intended to include such other forms of expression vectors which serve equivalent functions and which become known in the art subsequently hereto.

In addition, the nucleic acid according to the invention may also contain one or more additional regions, for example regulatory elements of small or large size which are available to the skilled artisan such as a promoter region (constitutive, regulated, inducible, tissue-specific, etc.), for example sequences allowing and/or promoting expression in the targeted tissue (e.g. choroid or retina) or cells (e.g. RPE or photoreceptors), a transcription termination signal, secretion sequences, an origin of replication and/or nuclear localization signal (nls) sequences which further enhance polynucleotide transfer to the cell nucleus. Such nls sequences have been described in the prior art including the SV40 large T antigen sequence.

Additionally, the nucleic acid may further comprise selectable markers useful in selecting, measuring, and monitoring nucleic acid transfer results (transfer to which tissues, duration of expression, etc.). The types of expression systems and reporter genes that can be used or adapted for use are well known in the art. For example, genes coding for a luciferase activity, an alkaline phosphatase activity, or a green fluorescent protein activity are commonly used.

The nucleic acid according to the invention may contain any nucleotide sequence of any size. The nucleic acid may thus vary in size from a simple oligonucleotide to a larger molecule such as a nucleotide sequence including exons and/or introns and/or regulatory elements of any sizes (small or large), a gene of any size, for example of large size, or a chromosome for instance, and may be a plasmid, an episome, a viral genome, a phage, a yeast artificial chromosome, a minichromosome, an antisense molecule, etc.

In a particularly preferred embodiment, the polynucleotide is a double-stranded, circular DNA, such as a plasmid, encoding a product with biological activity.

The nucleic acid can be prepared and produced according to conventional recombinant DNA techniques, such as amplification, culture in prokaryotic or eukaryotic host cells, purification, etc. The techniques of recombinant DNA technology are known to those of ordinary skill in the art.

In a particular embodiment, the nucleic acid of interest is capable of exerting a beneficial effect on the targeted cells. It may compensate for a deficiency in or reduce an excess of an endogenous substance. Alternatively, it may confer new properties on the targeted cells. It may be for example an antisense sequence or nucleic acid encoding a polypeptide which can affect the function, morphology, activity and/or metabolism of ocular cells.

The down regulation of gene expression using antisense nucleic acids can be achieved at the translational or transcriptional level. Antisense nucleic acids of the invention are preferably nucleic acid fragments capable of specifically hybridizing with a nucleic acid encoding an endogenous ocular active substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous ocular active substance. Antisense nucleic acids can be prepared by expression of all or part of a nucleic acid encoding an endogenous ocular active substance, in the opposite orientation. Any length of antisense sequence is suitable for practice of the invention so long as it is capable of down-regulating or blocking expression of the endogenous ocular active substance. Preferably, the antisense sequence is at least 20 nucleotides in length. The preparation and use of antisense nucleic acids, DNA encoding antisense RNAs and the use of oligo and genetic antisense is disclosed in WO92/15680, the content of which is incorporated herein by reference.

Among the biologically active polypeptides or proteins optionally expressed by a nucleic acid as described above and suitable for practice of the invention are enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, in particular soluble receptors, a peptide which is an agonist or antagonist of a receptor or of an adhesion protein, antigens, antibodies, fragments or derivatives thereof and other essential constituents of the cell, proteins involved in the visual cycle within RPE cells, and structure proteins of retinal cells (structure proteins, proteins involved in the phototransduction process and/or in the visual cycle; retinal recycling) and/or phagocytosis of the photoreceptor outer segment phagocytosis).

Various retina-derived neurotrophic factors have the potential to rescue degenerating photoreceptor cells, and may be delivered trough a method according to the present invention. Preferred biologically active agents may be selected from VEGF, Angiogenin, Angiopoietin-1, DeM, acidic or basic Fibroblast Growth Factors (aFGF and bFGF), FGF-2, Follistatin, Granulocyte Colony-Stimulating factor (G-CSF), Hepatocyte Growth Factor (HGF), Scatter Factor (SF), Leptin, Midkine, Placental Growth Factor (PGF), Platelet-Derived Endothelial Cell Growth Factor (PD-ECGF), Platelet-Derived Growth Factor-BB (PDGF-BB), Pleiotrophin (PTN), RdCVF (Rod-derived Cone Viability Factor), Progranulin, Proliferin, Transforming Growth Factor-alpha (TGF-alpha), PEDF, Transforming Growth Factor-beta (TGF-beta), Tumor Necrosis Factor-alpha (TNF-alpha), Vascular Endothelial Growth Factor (VEGF), Vascular Permeability Factor (VPF), CNTF, BDNF, GDNF, PEDF, NT3, BFGF, angiopoietin, ephrin, EPO, NGF, IGF, GMF, aFGF, NT5, Gax, a growth hormone, [alpha]-1-antitrypsin, calcitonin, leptin, an apolipoprotein, an enzyme for the biosynthesis of vitamins, hormones or neuromediators, chemokines, cytokines such as IL-1, IL-8, IL-10, IL-12, IL-13, a receptor thereof, an antibody blocking any one of said receptors, TIMP such as TIMP-1, TIMP-2, TIMP-3, TIMP-4, angioarrestin, endostatin such as endostatin XVIII and endostatin XV, ATF, angiostatin, a fusion protein of endostatin and angiostatin, the C-terminal hemopexin domain of matrix metalloproteinase-2, the kringle 5 domain of human plasminogen, a fusion protein of endostatin and the kringle 5 domain of human plasminogen, the placental ribonuclease inhibitor, the plasminogen activator inhibitor, the Platelet Factor-4 (PF4), a prolactin fragment, the Proliferin-Related Protein (PRP), the antiangiogenic antithrombin III, the Cartilage-Derived Inhibitor (CDI), a CD59 complement fragment, C3a and C5a inhibitors, complex attack membrane inhibitors, Factor H, ICAM, VCAM, caveolin, PKC zeta, junction proteins, JAMs, CD36, MERTK vasculostatin, vasostatin (calreticulin fragment), thrombospondin, fibronectin, in particular fibronectin fragment gro-beta, an heparinase, human chorionic gonadotropin (hCG), interferon alpha/beta/gamma, interferon inducible protein (IP-10), the monokine-induced by interferon-gamma (Mig), the interferon-alpha inducible protein 10 (IP10), a fusion protein of Mig and IP10, soluble Fms-Like Tyrosine kinase 1 (FLT-1) receptor, Kinase insert Domain Receptor (KDR), regulators of apoptosis such as Bcl-2, Bad, Bak, Bax, Bik, BcI-X short isoform and Gax, fragments or derivatives thereof and the like.

In a particular embodiment, the nucleic acid encodes a soluble fragment of the TNF[alpha] receptor, the TGF[beta]2 receptor, of VEGFR-1, VEGFR-2, VEGFR-3, CCR2 or MIP1. The nucleic acid may also, in another preferred embodiment, encode an antibody, a variable fragment of a single-chain antibody (ScFv) or any other antibody fragment having recognition capacities for the purposes of immunotherapy.

In a particular embodiment of the present invention, the biologically active nucleic acid encodes a precursor of a therapeutic protein usable in the present invention such as those described above.

In another particular embodiment, the method of the invention is particularly suitable for performing gene replacement. Accordingly the nucleic acid may encode for a viable protein so as to replace the defective protein which is naturally expressed in the targeted tissue. Typically, defective genes that may be replaced include, but are not limited to, genes that are responsible for retinal degenerative diseases such as retinitis pigmentosa (RP), Leber congenital amaurosis (LCA), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, and Birdshot Retinochoroidopathy. Examples of genes include but are not limited to genes encoding for ATP-binding cassette transporter, RPE65, RdCVF, CP290.

In another embodiment, the method of the invention is particularly suitable for performing exon skipping for restoring the function of mutated proteins responsible for retinal degenerative disease. Exon skipping involves blocking or preventing the incorporation into mature mRNA of one or more targeted exon(s) which encodes amino sequences that are responsible for a protein dysfunction. This is accomplished by exposing the pre-mRNA that includes exons encoding the protein to antisense oligonucleotides (AONs) which are complementary to sequence motifs that are required for correct splicing of the one or more targeted exons. The AONs bind to complementary required sequences in the pre-mRNA and prevent normal splicing. Instead, the targeted exons are excised and are not included in the mature mRNA that is translated into protein, and the amino acid sequences encoded by the targeted exons are missing from the translated protein.

Furthermore, in another embodiment of the present invention, a mixture of nucleic acids encoding distinct biologically active products can be used. This variant allows co-expression of different products in the ocular cells.

The pharmaceutical composition of the invention may also comprise compatible or physiologically acceptable carrier, excipient or diluent.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Pharmaceutically compatible or physiologically acceptable carrier, excipient or diluent includes diluents and fillers which are pharmaceutically acceptable for the methods of the invention, are sterile, and may be selected from neutral to slightly acidic, isotonic, buffered saline (including phosphates, chloride, etc.), aqueous or oleaginous solutions or suspensions and more preferably from sucrose, trehalose, surfactants, proteins and amino acids. The pharmaceutically compatible or physiologically acceptable carrier, excipient or diluent is preferably formulated using suitable dispersing, wetting, suspending, soothing, isotonic or viscosity building agents, stabilizers, preservatives and appropriate buffers to form an isotonic solution. The particular pharmaceutically acceptable carrier and the ratio of active compound to carrier are determined by the solubility and chemical properties of the composition, the particular mode of administration, and standard pharmaceutical practice. Those skilled in the art will understand how to formulate such vehicles by known techniques.

An example of stabilizers is disodium edetate or the like. Examples of isotonic agents are glycerin, propylene glycol, polyethylene glycol, sodium chloride, potassium chloride, sorbitol and mannitol or the like. Examples of buffers are citric acid, sodium hydrogenphosphate, glacial acetic acid and trometamol or the like. Examples of pH adjusters are hydrochloric acid, citric acid, phosphoric acid, acetic acid, sodium hydroxide, sodium carbonate and sodium hydrogencarbonate or the like. An example of soothing agents is benzyl alcohol or the like. Examples of preservatives are benzalkonium chloride, benzethonium chloride, p-hydroxybenzoate esters, sodium benzoate and chlorobutanol or the like.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from about 0.01 to about 2 wt. %.

Preparation forms of the pharmaceutical composition intended for administration to suprachoroidal space are preferably liquid preparations. The liquid preparations can be prepared, for example, by dissolving the biologically active agent in BSS (Balanced Salt Solution), a glycerin solution, a hyaluronic acid solution and the like. A particular composition comprises for example BBS (60%) and hyaluronic acid (40%). A stabilizer, an isotonic agent, a buffer, a pH adjustor, a soothing agent, a preservative, electrolytes, such as sodium, potassium, calcium, magnesium and/or chloride or the like can optionally be added in an adequate amount to the liquid preparations.

The pharmaceutical composition may comprise or the biologically active agent may be combined (in a use according to the present invention) with any additional active ingredient or adjuvant. The adjuvant may be selected from any substance, mixture, solute or composition facilitating or increasing the biological activity of the prophylactic or therapeutic agent such as any biologic, synthetic or biosynthetic agent which improves the delivery or transfer of said agent and may be assimilated to a vector (as delivery carrier) according to the invention. The adjuvant may be conditioned and administered separately or sequentially from the prophylactic or therapeutic agent containing composition and/or at a distinct site of injection. Treatment with multiple agents and/or adjuvants according to the invention need not be done using a mixture of agents and/or adjuvants but may be done using separate pharmaceutical preparations. The preparations need not be delivered at the same exact time, but may be coordinated to be delivered to a patient during the same period of treatment, i.e., within a week or a month of each other.

Any suitable therapeutic agents can be coordinated with the compositions of the present invention. Non-limiting examples of therapeutic agents which may be administered in addition to the above biologically active (prophylactic or therapeutic) agent(s) through a method according to the present invention also include permeabilizing agents such as a virus, a lipid vesicle, hyaluronic acid, lipid-based positive ions, polycationic emulsions, cationic peptides, polyplex, etc.; antibiotics and antimicrobial agents such as tetracycline hydrochloride, leucomycin, penicillin, penicillin derivatives, erythromycin, sulphathiazole and nitrofurazone; local anesthetics such as benzocaine; vasoconstrictors such as phenylephrine hydrochloride, tetrahydrozoline hydrochloride, naphazo line nitrate, oxymetazoline hydrochloride and tramazoline, hydrochloride; cardiotonics such as digitalis and digoxin; vasodilators such as nitro-glycerine and papaverine hydrochloride; antiseptics such as chlorhexidine hydrochloride, hexylresorcinol, dequaliniumchloride and ethacridine; enzymes such as lysozyme chloride and dextranase; hypotensives; sedatives; anti-tumor agents; steroidal anti-inflammatory agents such as hydro-cortisone, prednisone, fluticasone, prednisolone, triamcinolone, acetonide, dexamethasone, betamethasone, beclomethasone, and beclomethasone dipropionate; non-steroidal antiinflammatory agents such as acetaminophen, aspirin, aminopyrine, phenylbutazone, mefanamic acid, ibuprofen, diclofenac sodium, indomethacin, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents; and analgesic compounds.

Actual dosage levels of active ingredients in the compositions of the present invention may be adapted so as to obtain an amount of active ingredient that is effective to obtain a desired biological activity. It should be understood, however, that the specific dose level for any particular patient will depend upon a variety of factors including the body weight, general health, sex, diet, time, rates of absorption and excretion, combination with other drugs and the severity of the particular disease being treated.

The means to inject the pharmaceutical composition into the suprachoroidal space may be an injection needle or preferably a flexible catheter or microcannula. Methods for injecting a pharmaceutical injection into the suprachoroidal space are well known in the art (e.g. Einmahl S. Invest Ophtamol Vis Sci 2001 42:695: Galimova V U. Vestn Oftalmo 2001 117:20; Olsen T W Am J. Ophtalmol 2006 142:777). Devices for injecting a pharmaceutical composition into the suprachoroidal space are also well known in the art (e.g. Olsen T W Am J. Ophtalmol 2006 142:777, US 2010173866, WO 2007100745 and WO 2011053512).

Exposing the region where the pharmaceutical composition was delivered to an electrical field may be performed through an extra ocular electroporation. Electroporation is indeed suitable for, or increase, permeability of a cell membrane and/or at least a portion of a targeted tissue adjacent to the suprachoroidal space to a biologically active agent such as a nucleic acid. In addition, a brief electric impulse with a given field strength is used to allow transport or migration of agents through the tissue or across cell membranes into cells, by an electrophoretic effect. The technique of electroporation is well known to those of ordinary skill in the art. However, to date electroporation failed to transfect adult photoreceptor cells when the plasmids were injected either into the ocular cavity or into the sub retinal space.

In a particular embodiment, an electrical field constituted of one or more electrical pulse(s) is applied.

The field intensity of which is between about 1 and 600 volts, preferably 1 and 400 volts, even more preferably between about 1 and 200 volts, advantageously between about 10 and 100 volts, or 15 and 70 volts.

The total duration of application of the electric field may be between 0.01 millisecond and 1 second, preferably between 0.01 and 500 milliseconds, more preferably between 1 and 500 milliseconds, even more preferably greater than 1 or 10 milliseconds. In a preferred embodiment, the total duration of application of the electric field is between 10 milliseconds and 100 milliseconds and is preferably of 20 milliseconds.

Electric pulses applied may be between for example 1 and 100 000. Their frequency may be comprised between 0.1 and 1000 hertz. It is preferably a regular frequency.

Electric pulses may also be delivered in an irregular manner relative to each other, the function describing the intensity of the electric field as a function of the time for one pulse being preferably variable.

Electric pulses may be unipolar or bipolar wave pulses. They may be selected for example from square wave pulses, exponentially decreasing wave pulses, oscillating unipolar wave pulses of limited duration, oscillating bipolar wave pulses of limited duration, or other wave forms. Preferentially, electric pulses comprise square wave pulses or oscillating bipolar wave pulses.

In the present invention, when choroid is targeted, the electrical field is applied by using two electrodes, one of said electrodes being introduced into the suprachoroidal space and the other one is applied on the surface of the sclera at the opposing side where the suprachoroidal injection was performed.

Alternatively when retina is targeted, two embodiments are possible. In a first embodiment the electrical field is applied by using two electrodes, one of said electrodes being introduced into the suprachoroidal space and the other one is applied on the surface of the eye at the opposing side where the suprachoroidal injection was performed. In a second embodiment, the electrical field is applied by using two electrodes, one of said electrodes is applied on the surface of the sclera adjacent to the region where the suprachoroidal injection was performed and the other one is applied on the surface of the eye (e.g. sclera or conjunctiva) at the opposing side where the suprachoroidal injection was performed.

Electrodes are preferably chosen from a wire type electrode and a plate contact type electrode, each type of electrode being optionally adapted to be reversibly applied on the surface of eye. Preferably the plate contact type electrode is curved.

In a particular embodiment, the plate-contact electrode is preferably made of a rigid material and of a curved form adapted to the geometry of the surface of the sclera or eye (e.g. conjunctiva). Electrodes are advantageously made of a conductive non oxidative metal selected for example from iridium or platinum Typically, the electric field is applied with means of devices as described in the example.

The method of the present invention is particularly suitable for the treatment of ocular diseases affecting the posterior region of the eye, and more particularly ocular diseases affecting the choroid, retina or neuroretina. Non-limiting examples of ocular diseases that may be treated by the method of the present invention include ocular diseases affecting the macula such as age related macular degeneration (wet and dry) or inherited macular degeneration, macular oedema of any origin (age related macular degeneration, diabetes, inflammation, degeneration, central serous chorioretinitis or diffuse epitheliopathy . . . ), inherited retinal dystrophies, such as Leber congenital amaurosis, retinitis pigmentosa, cone rod dystophies, best vitelliforme maculopathy, intraocular inflammation such retinitis, chorioretinitis, choroiditis, ischemic retinopathy (in particular retinopathy of prematurity and diabetic retinopathy), retinal vascular diseases, ocular ischemia syndrome and other vascular anomalies, choroidal disorders and tumors, vitreous disorders, glial proliferation such as proliferative vitreo retinopathy and glial proliferation associated to diabetic pre retinal angiogenesis, diabetic retinopathy ischemic or proliferative.

Inherited retinal dystrophies or retinitis pigmentosa are inherited blinding diseases due to mutations or deletions in genes implicated in the visual cycle. They begin at a young age and progress slowly until total blindness. Loss of photoreceptors is associated with loss of retinal pigment cells and to vascular and optic nerve atrophy at the later stages. Some of these inherited degeneration are due to mutation in mitochondrial DNA. In particular, non limiting examples of retinal degenerative diseases include but are not limited to retinitis pigmentosa (RP), Leber congenital amaurosis (LCA), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, and Birdshot Retinochoroidopathy.

Intraocular inflammation regroups all types of inflammation of the intraocular tissues, mainly uvea and retina. Intraocular inflammations may be from immunologic causes, infectious causes, iatrogenic causes or of unknown etiologies. They may be acute, recurrent or chronic. Intraocular inflammations are among the most common causes of curable blindness. Posterior segment intraocular inflammations may be associated with vasculitis, optic neuritis, vitritis and chorio retinitis, retinitis, choriditis, choroidal neovascularisation, choroidal neovascularization due to AMD, to myopia, inflammation, diffuse epitheliopathy, bruch membrane rupture, polypoidal choroidal vasculopathy, post traumatic.

There are two major types of glaucoma: chronic glaucoma or primary open-angle glaucoma (POAG) and acute closed-angle glaucoma. Other variations include congenital glaucoma, pigmentary glaucoma, neovascular glaucoma and secondary glaucoma. Glaucoma is similar to ocular hypertension but with accompanying optic nerve damage and vision loss. Glaucoma is usually treated with eye drops, laser, or conventional eye surgery. If not treated, glaucoma will cause blindness.

Angiogenesis is the formation of new capillary blood vessels leading to neovascularization. Angiogenesis is a complex process which includes a series of sequential steps including endothelial cell mediated degradation of vascular basement membrane and interstitial matrices, migration of endothelial cells, proliferation of endothelial cells, and formation of capillary loops by endothelial cells. Though angiogenesis is a normal process for the development or maintenance of the vasculature, pathological conditions (i.e., angiogenesis dependent diseases) arise where blood vessel growth is actually harmful. Angiogenesis is notably associated with important diseases of ocular tissue, including diabetic retinopathies, age related macular degeneration, retinopathy of prematurity, corneal graft rejection, neovascular glaucoma and corneal scaring. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

Diabetic Retinopathy occurs when the retinal vessels inside the eye leak blood and fluids into the surrounding tissue. About 80% of patients with diabetes develop diabetic retinopathy. This disease is generally treated using a laser. However, laser therapy involves complications including retinal vein occlusion, loss of visual acuity, vitreous hemorrhage and sometimes failure. If left untreated, diabetic retinopathy may cause blindness.

Retinopathy of Prematurity (ROP) affects prematurely born babies. It consists of the abnormal growth of blood vessels within the retinal and vitreous. Progression to later stages of ROP can lead to the formation of scar tissue on the retina, vitreous hemorrhage, and retinal detachment. The treatment is usually performed either by laser or cryotherapy (freezing).

Ischemic retinopathies are retinopathies associated with vascular occlusion (capillaries or large vessels) that lead to neuroretinal suffering, cell death and neo angiogenesis. Macular degeneration is a disease that affects central vision and leads to loss of vision. Although there are forms of macular degeneration that strike young people, the condition occurs most commonly in people who are over 60 years of age. This disorder is thus called age-related macular degeneration (AMD). Because only the center of a person's vision is usually affected, blindness rarely occurs from the disease. However, injury to the macula in the center of the retina can destroy the ability to see straight ahead clearly. Dry forms associate degeneration of neuroretina, RPE cells and choroids. Wet forms associate previously described phenomenons and growth of neovessels from the choriocapillaries and/or retinal vessels, sub retinal detachment and hemorrhages, sub epithelial hemorrhages and tears, etc. Macular degeneration usually occurs after the age of sixty. While your central vision is reduced, most patients retain some vision and never go totally blind.

A particular aspect of the invention is a method of treating intraocular neovessels or macular oedema comprising delivering to the suprachoroidal space of a subject suffering therefrom a nucleic acid encoding an anti VEGF, an anti VEGF receptor or an anti PLGF.

A further particular aspect of the invention is a method of treating or delaying retinitis pigmentosa comprising delivering to the suprachoroidal space of a subject suffering therefrom a nucleic acid encoding a neurotrophic factor as described above.

Another particular aspect of the invention is a method of treating diabetic retinopathy comprising delivering to the suprachoroidal space of a subject suffering therefrom a nucleic acid encoding an anti IRS-1 or IGF-1.

In accordance with the methods of the present invention, kits for preventing or treating an ocular disease are envisioned. Devices and pharmaceutical composition according to the present invention may be supplied together in a kit. Within the kit, the components may be separately packaged or contained. Other components such as excipients, carriers, other drugs or adjuvants, instructions for administration of the active substance or composition, and administration or injection devices can be supplied in the kit as well. Instructions can be in a written, video, or audio form, can be contained on paper, an electronic medium, or even as a reference to another source, such as a website or reference manual.

The invention will be further illustrated by the following figures and examples. However, these examples and figures should not be interpreted in any way as limiting the scope of the present invention.

Example

Material & Methods

Animals

Eight to ten weeks old female albino Lewis rats (Elevage Janvier, Le Genest Saint Isle, France) were used in most the experiments and handled in accordance with the ARVO Statement for the Use of Animals in Ophthalmic and Vision Research. For fluorescein angiography follow-up, 8-10 weeks male pigmented Brown-Norway rats (Charles River, L.'Arbresle, France) were used. Rats were anesthetized by intramuscular injection of ketamine (75 mg/kg) (Virbac, France)+largactil (0.5 mg/kg) (Sanofi-Aventis, France). At the end of the experiments, animals were sacrificed by carbon dioxide inhalation.

Plasmids

The commercially available pVAX1 LacZ plasmid encoding for the β-galactosidase reporter gene, under the control of a cytomegalovirus (CMV) promoter (6 kbp, 25 nm, Invitrogen, Carlsbad, Calif., USA) was used to localize gene expression after suprachoroidal injection followed or not by electrotransfer. The pVAX2-sFlt-1 plasmid (4.9 kbp), encoding the rat soluble vascular endothelial growth factor receptor-1 (sFlt-1), was constructed after isolation and reverse transcription of the sFlt-1 mRNA extracted from rat placenta followed by amplification and subcloning of the cDNA downstream of the in the CMVβ promoter in the pVAX2 backbone. Its sequence has been checked by DNA sequencing and it has been validated in a rat model of choroidal neovascularization after delivery through ciliary muscle electrotransfer. In this study, it was used to evaluate its efficacy through suprachoroidal electrotransfer delivery in the same model. The non-coding pVAX1 and pVAX2 plasmids backbone were used as negative controls. Plasmids were amplified in *Escherichia coli* bacteria and prepared endotoxin-free (EndoFree Plamid Kit; Qiagen, Courtaboeuf, France). Plasmids were diluted in endotoxin-free (EF) water containing 77 mM of NaCl (half saline) (saline, NaCl 0.9%, Versol∀, Laboratoire Aguettant, Lyon, France) as previously described [24]. The concentration of DNA was determined by spectroscopy measurements (optical density at 260 nm).

Injection of DNA into the Suprachoroidal Space

Plasmid DNA (30 µg), vehicle (half-saline) or Mayer.'s hemalun solution were injected into the suprachoroidal space using a curved 30 G disposable needle (Micro-Fine+ Demi syringue, 0.30×8 mm, BD Biosciences, Le Pont de Claix, France) and under a volume of thirty microliters (unless stated otherwise). Injection was performed in the temporal hemisphere of the eye at 1 mm posterior to the limbus. After perforating the sclera, the needle could be easily visualized in the suprachoroidal space. Injection was performed slowly to progressively induce opening of this virtual space.

Electrotransfer to the Suprachoroidal Space

Immediately after injection of plasmid DNA into the suprachoroidal space, the inoculated area was submitted to an electrical field using the device presented as Device 2. A contact curved platinum/iridium sheet (anode, +) was attached to the sclera, just above the injected area. A semi-annular platinum/iridium sheet (cathode, −) was placed on the sclera, facing the anode at the opposing side of the eye. All electrodes were home made from platine folds purchased from Good Fellow (Lille, France). Electrotransfer was performed by applying 8 square waves electrical pulses (20V voltage, 20 ms duration, 5 Hz frequency) generated by the 830 BTX electropulsator (Genetronics, san Diego, Calif.). This standard procedure (device and electrical parameters) was used in most experiments, except those designed to evaluate other electrical devices or other electrical parameters (see Results section for details).

Eye Fundi Examinations

Immediately after suprachoroidal injection, eye fundi were examined under an operating microscope, using a coverslide applied on the corneal surface, to evaluate the accurate placement of the injection and to ensure that no area of retinal detachment has occurred. Photos were taken using a numeric camera (Coolpix, Nikon, Fnac, Paris, France). Fluorescein angiography was performed on anesthetized pigmented rats 3 days after treatment, before choroidal neovascularization induction (see "Therapeutic application." section). For this purpose, pupils were dilated with 1% tropicamide and fluorescein (0.2 mL of 10% fluorescein in saline) was administered intravenously. Angiograms were established in the temporal treated area and at the optic nerve head using a confocal scanning laser ophthalmoscope (cSLO) (HRA, Heidelberg Engineering, Dossenheim, Germany) [32].

Histological Analysis of Suprachoroidal Detachment

Two to five minutes after suprachoroidal injection of Mayer.'s hemalun solution, eyes were enucleated and fixed with a mixture of 4% paraformaldehyde and 0.5% glutaraldehyde in phosphate buffered saline (PBS) for 2 hours at room temperature. They were rinsed for 2 hours in PBS, dehydrated at room temperature with increasing ethanol concentrations before being incubated overnight at 4° C. with infiltration solution provided in the Leica Historesin Embedding kit. Samples were embedded in resin (Leica) and 5-μm thick histological sections were performed along the naso-temporal plane of the eye using a microtome (Leica). Sections were stuck on gelatin-coated slides, stained for 2 min with 1% toluidin blue solution and observed by light microscopy under an Aristoplan light microscope (Leica, Rueil-Malmaison, France) coupled with a Leica DFC480 camera.

β-galactosidase Activity Visualization

To localize β-galactosidase gene expression in ocular tissues, eyes were enucleated 7 days, 14 days, 1 month or 4.5 months after suprachoroidal electrotransfer of the pVAX1 LacZ. pVAX1 backbone was used as control. Freshly enucleated eyes were incised at the limbus and fixed for 1 h at 4° C. in PBS containing 2% paraformaldehyde and 0.2% glutaraldehyde. They were rinsed three times in PBS before being incubated overnight at room temperature with 1 mg/mL X-gal (5-bromo-4-chloro-3-indolyl galactopyranoside; Sigma-Aldrich, Saint-Quentin Fallavier, France) in PBS containing 5 mM of $K_3Fe(CN)_6$, 5 mM of $K_4Fe(CN)_6$, 2 mM of $MgCl_2$ and 0.02% NP40, as detailed previously [33]. After washing with PBS, direct imaging from the outside of the eyes was realized using a numerized camera (Coolpix, Nikon, Fnac, Paris, France).

Analyses were then carried out on histological sections and flatmounts. For histological analyses, eyeballs were dehydrated at room temperature with increasing ethanol concentrations before being embedded in paraffin. Naso-temporal sections (10 μm-thick) performed in the blue colored areas expressing the β-galactosidase reporter gene were counterstained with hematoxilin-eosin and observed by light microscopy under an Aristoplan light microscope (Leica, Rueil-Malmaison, France) coupled with a Leica DFC480 camera.

For flatmount analyses, eyes were carefully dissected by transversal section at 1 mm from the limbus. Anterior segments were discarded and the neuroretinas were carefully separated from the remaining RPE-choroid-sclera complexes. Neuroretinas and RPE-choroid-sclera complexes were flat-mounted separately in PBS/glycerol (1/1, v/v) and observed under an operating microscope using a numerized camera (Coolpix, Nikon, Fnac, Paris, France).

Electroretinography (ERG)

For full field ERG recordings, rats were anesthetized by intramuscular injection (0.8-1.2 ml/kg) of a solution containing ketamine (40 mg/ml) and xylazine (4 mg/ml, Rompun). Animals were light adapted for 10 minutes with a background light of 25 cdm2 cd#s/m2. The cornea was desensitized with a drop of Novesine (Novartis Ophthalmics) and the pupils were dilated with a drop of Tropicamide (Novartis Ophthalmics). Gold wire ring electrodes placed on the corneas of both eyes and electrodes inserted into the forehead served as working electrodes and reference electrodes, respectively. A stainless steel needle electrode was inserted into the tail of the animals for grounding. All the manipulations were performed under dim red light, Measurements were performed using the commercial VisioSystem device (Siem Biomedicale).

Light flashes were then applied, the light intensity of the flash being 10 cd·s/m2. Five recordings were averaged with an interstimulus interval of 10 seconds. Amplitudes of awaves and b-wave were measured (in μ(V) and data obtained from each eye belonging to the same experimental group were averaged.

Therapeutic Application

Choroidal neovascularization was induced by laser photocoagulation in Brown Norway untreated control eyes or in eyes treated three days before by temporal suprachoroidal electrotransfer of 30 μg of pVAX2 or pVAX2-sFlt-1. A 532 nm argon laser (Viridis 532 nm, Quantel Medical, Clermont-Ferrand, France) mounted on a slit lamp (Hagg-Streitt, BQ 900) was used throughout. A glass coverslip fulfilled the role of a contact lens during the laser delivery. Eight laser spots (100 μm spot size, 0.1 s duration and 175 mW power) were performed per eye, with 4 lesions in the temporal retina and 4 lesions in the nasal retina. The reactive bubble observed at the retinal surface after laser delivery was considered as an evidence of the appropriate focusing and as an indication of the rupture of Bruch.'s membrane.

Eyes were enucleated 15 days after CNV induction and immediately fixed for 15 min with paraformaldehyde (PAF) 4% solution in PBS. After washing in PBS, RPE-choroid-sclera complexes were carefully separated from the neuroretinas and post-fixed with methanol 100% for 15 min at −20° C. Tissues were rehydrated in PBS containing 1% Triton X-100 and incubated overnight with lectin from *Bandeiraea simplicifolia* conjugated to fluorescein isothiocyanate (Lectin, FITC labeled, from *Bandeiraea simplicifolia*, BS-I, Ref. L9381, Sigma Aldrich). After washing in PBS, tissues were flat mounted using gel mount (Biomeda Corp., VWR, Fontenay-sous-Bois, France) and observed by fluorescence microscopy using an Olympus BX51 microscope. Photographs were taken using the same exposure times and contrast settings. CNV areas (in $\mu m_2$) were determined by FITC-lectin fluorescence and measured by outlining the margins of the labeled area on flat mounts images using the ImageJ software. The measurements of neovascular area obtained from multiple lesions were averaged into a single value for each eye.

Statistical Analysis

For each experiment, the number of eyes treated per condition was written in the legend of the figures. For numerical data, results were expressed as means±standard error of the mean (SEM) and compared using the non-parametric Mann-Whitney U test (Prism 4.0, Graph Pad Software Inc., San Diego, Calif.). $p<0.05$ was considered significant.

Results

Suprachoroidal Injection

To validate injections into the suprachoroidal space, i.e. between the sclera and the underlying choroids, the procedure was first monitored in vivo using Mayer.'s hemalun solution. Diffusion of the dye into the suprachoroidal space during injection could be visualized in real time from the external side of eyes from albinos rats. When the injection needle was removed after the injection was over, a colored circle area corresponding to the putative area of suprachoroidal pocket could be observed from outside the eye. No subretinal bleb, corresponding to a detachment between photoreceptor outer segments (OS) and retinal pigment epithelial cells (RPE) could be noticed on eye fundus, the dye being localized deeper into the suprachoroidal space. To confirm these macroscopic observations, resin histological sections were performed on eyes fixed a few minutes after the injection. A detachment between the choroid and the sclera could be highlighted, keeping the whole neural retina adherent to retinal pigment epithelial (RPE) cells that still adhered to bruch.'s membrane and choriocapillary/choroid. The detachment spread on the half anterior part of the temporal hemisphere. It was large and complete in the anterior part, next to the needle insertion site, and progressively decreased posteriorly, with apparent focal attachments between the choroid and the sclera. Observations made posteriorly to the suprachoroidal detachment showed that the choroids was in close contact with the sclera, as observed in untreated control eyes. No hemorrhage could be noticed in any of the eyes (n=5). In all of the following experiments, eye fundus examination was performed after the injection to exclude from the analysis eyes with bubble of retinal detachment. Only two eyes among all treated eyes were excluded from the analysis because of accidental subretinal injection. Note that no bleeding or hemorrhages were noted during or immediately after the surgery, nor 7 days after injection alone. Very faint or no β-galactosidase activity was observed 7 days after the simple suprachoroidal injection of pVAX1-LacZ plasmid DNA and no blue coloration was found with the pVAX1 plasmid backbone, demonstrating that no or very poor tranfection occurs with injection alone.

Electrical Devices for Suprachoroidal Electrotransfer (ET)

Immediately after plasmid injection (30 μg in 30 μl of pVAX1-LacZ) in the suprachoroidal space, the injected area was submitted to an electric field (electrotransfer procedure), created by the application of different electrode shape and placement. The electric field was created using 8 pulses of 20V voltage intensity and 20 ms duration, with a frequency of 5 Hz. Compared to injection alone, β-galactosidase gene expression was significantly enhanced by ET with all the tested electrodes. However, each device exhibited different transfection efficacy. In preliminary experiments, the device used was the one that has been developed in our laboratory to transduce ocular ciliary muscle fibers in vivo by ET [24], with some adaptations regarding the positioning of both electrodes. A platinum/iridium (Pt/Ir) wire (250 μm in diameter, negative pole) was inserted in the suprachoroidal space, after the needle of injection was withdrawn, facing a semi-annular Pt/Ir sheet (anode electrode) attached to the sclera at the opposing side of the injection site. In such conditions, the area of tissue expressing β-galactosidase observed from outside the eye appeared as a line corresponding to the site where the wire electrode had been inserted. To extend plasmid DNA cellular uptake and expression, we decided to use larger electrodes and to place them externally. When a semi-annular Pt/Ir sheet (anode) was placed on the scleral surface located above the inoculated area with a semi-annular Pt/Ir wire electrode (cathode) positioned on the scleral surface, at the base of the posterior pole of the eye (Device 1), β-galactosidase expression was localized in the anterior part of the posterior segment, where the sheet electrode was located. When a contact curved platinum/iridium sheet (anode, +) was attached to the sclera above the injected area with a semi-annular platinum/iridium sheet (cathode, −) placed on the sclera, facing the anode at the opposing side of the eye (Device 2), the area of tissue expressing the β-galactosidase reporter gene was greatly extended as compared with the two other devices. With such a device, the anode covered the whole area of suprachoroidal detachment and reporter gene was expressed in almost the whole detached surface, except for the little zone where no electrical field was generated and corresponding to the plastic connecting forceps placed on the eye surface to maintain the contact curved electrode. No blue coloration could be observed in eyes treated by ET of the pVAX1 backbone, whatever the electrical device used. No hemorrhage was noticed during electrical field application or 7 days after ET.

Optimal Electrical Parameters for Suprachoroidal Electrotransfer

Using device 2 several set of electrical parameters were tested after injection of 30 μg (in 30 μl) of pVAX1-LacZ into the suprachoroidal space, varying in voltage intensity (V) and pulse duration (ms). Seven days after treatment, transfection efficacy visualized by β-galactosidase expression (blue coloration) was not different in eyes submitted to eight pulses of 7V (20 ms, 5 Hz) than that obtained in eyes treated by injection alone. On the contrary, application of eight pulses (20 ms, 5 Hz) with a voltage intensity of 15V, 30V and 60V significantly enhanced β-galactosidase expression compared to eyes treated by injection alone. Transfection efficacy increased with increasing voltages, the better efficacy being obtained with 30V. Using this condition, reporter gene expression could be detected in almost the whole temporal hemisphere. We demonstrated otherwise that reporter gene activity was as, even more, efficient using a 20V voltage than using a 30V voltage.

As judged by paraffin histological section analysis, retinal morphology was well preserved in eyes submitted to voltages inferior or equal to 30V compared to control eyes treated by injection alone. Indeed, retinal layers had similar organization and thicknesses in the areas transfected by means of electrical field application to that observed in areas injected only. However, application of a 60V voltage induced a marked retinal disorganization of all retinal layers and an increase in retinal thickness maybe induced by an edema phenomenon. Note that no hemorrhage could be detected 7 days after electrical field application, whatever the voltage considered. Thus, electrical field application seemed to be safe under selected conditions, at least to the retinal morphology point of view. Since the lowest voltage consistent with safe and effective gene transfer was 20V, further experiments were performed using this parameter.

With respect to pulses duration, transfection efficacy was significantly higher using pulses of 20 ms than that of 10 ms (both at 20V and 30V, not shown), explaining why this duration has been chosen in further experiments. Regarding the volume of injection, preliminary experiments had demonstrated that volumes of 30 µl (or 40 µl) were required to achieve a good transfection efficacy when combined with ET (30V, 20 ms, 5 Hz) and that smaller volumes like 20 µl were not adapted (not shown). Using 30 µL, the area of suprachoroidal detachment was larger allowing transfection to be more extended and more reproducible. No detectable difference could be observed between all volumes using injection alone.

Efficacy of Suprachoroidal Electrotratransfer

Low magnification observation of flat-mounted RPE-choroid-sclera complexes and neuroretinal show that choroidal cells and vessels have been transfected as well as neuronal tissues. Histological sections confirmed the β-galactosidase activity in choroidal cells including choroidal vessels, but also showed activity in RPE cells and in photoreceptors outer and inner segments. Larger magnification confirms transfection of choroidal vessels, regular transfection of RPE cells and β-galactosidase activity in outer and to a lesser extent in inner segments of the photoreceptors. Using phase contrast analysis of unstained sections, the blue coloration resulting from β-galactosidase activity was better detected in choroidal cells including choroidal vessels, in RPE cells and at higher magnification around photoreptor nuclei and in inner segments, suggesting that photoreceptors were transfected.

Duration of Transgene Expression

β-galactosidase activity was maximal on day 7 (first time point tested) when transfection was detected in the whole area corresponding to the area of suprachoroidal detachment. Then, gene expression decreased over time from day 7 to 4.5 months, both at the intensity level and extent level. Compared to the observations made at day 7, staining was less uniform at day 14 even if still strong. One month after electrotransfer, β-galactosidase activity was faint with most expression following a circular ring, corresponding to the edges of the suprachoroidal detachment bleb. After 4.5 months, reporter gene expression was still detectable only in a restricted area. No pathological changes were noted externally or in eye fundus during the observation period. Using a CMV promoter, a significant expression was achieved for at least a month and then decreased until 4.5 months Safety of the Procedure To evaluate the possible changes induced by the suprachoroidal injection and electrotransfer procedure on the choroidal and retinal vasculatures, fundi angiographies were performed 3 days after treatment with the plasmid backbone. No vascular leakage or window effects could be observed in the temporal treated areas compared the same area of untreated control eyes demonstrating that treatment apparently maintained the integrity of the vessels and RPE. Moreover, no leaky vessel could be detected at the optic nerve head level in both groups suggesting no major early hemato retinal barrier breakdown. To analyze whether the procedure of suprachoroidal injection and electrotransfer had functional consequences on retinal electrophysiological, ERGs were recorded 7 days after treatment. In comparison to untreated control eyes, injection alone of vehicle solution (half-saline) did not induce any significant modification of a- and b-wave amplitudes. Furthermore, no statistical difference in a- and b-wave amplitudes could be detected between eyes submitted to electrotransfer after vehicle injection and eyes treated by injection alone or untreated control eyes. Moreover, no intraocular inflammation could be noticed by clinical examination at the same time point.

Therapeutic Efficacy

The anti anti-angiogenic efficacy of the suprachoroidal electrotransfer of a plasmid encoding the rat soluble vascular endothelial growth factor receptor-1 (sFlt-1) was evaluated in a rat model of choroidal neovascularization (CNV). In all groups, no statistical difference in CNV area could be noticed between the temporal and the nasal sides, explaining why all the values measured per eye were averaged into a single one. As shown by observation and quantification of neovascular areas performed at the peak of the disease, a significant reduction plus que 25% of laser-induced CNV area was observed in rats treated by electrotransfer of the therapeutic plasmid (18 500±1430 µm2) compared to control eyes treated by electrotransfer of the corresponding empty plasmid (25 100±1710 µm2) and to untreated control eyes (25 700±1 400 µm2). Moreover, no exacerbation of CNV could be noticed in pVAX2 treated eyes compared to untreated control eyes.

Discussion

We have already demonstrated that suprachoroidal administration is a safe and reproducible procedure, allowing the depot of a slow release polymer [25]. Since, other groups have confirmed the feasibility of this route of administration and particularly the group of T. Olsen has developed an elegant suprachoroidal catheter equipped with a lighting system to follow the adequate placement of the injector up to the posterior pole [26]. In the present study, we demonstrate that this route can also be used to deliver plasmid DNA in the choroid and adjacent retinal cells and that the plasmids remained confined in this space longer enough to allow their transduction by ab externo application of an electrotransfer current. Due to the very high blood flow in the choroid, one could have anticipated that plasmids in a solution would have been washed away within seconds. However, the adequate injection in the suprachoroidal space probably creates a "pocket" in which the plasmid solution is trapped and maintained a pressure on RPE cells for a time sufficient to allow the transfection. How plasmid DNA can reach RPE cells through the Bruch membrane is not clear since molecule higher than 300 KD are not suppose to cross it [27]. However, it was shown that lipoprotein particles of 20-30 nm originating from the retina were found in the Bruch membrane, particle in the size range of plasmid [28]. The more unexpected observation was that not only RPE cells but also photoreceptors were transfected. Similar results have just been published after the suprachoroidal administration of an AAV in the rabbit eye [29]. Further studies are required to analyze the transport mechanisms responsible for the plasmid diffusion from the suprachoroidal space to the RPE cells and the neuroretina. Interestingly, even when the subretinal injection of plasmid was performed combined with electroporation in adult animals, photoreceptors were not transfected [22, 23]. This can be related to the different current field we have created using different electrode shape and placement. In addition to the injection, the electric field is crucial for electroporation to occur as shown by the absence of transfection when the plasmid was injected without current application. Appropriate parameters must be adapted for each tissue to define the efficacy and toxic thresholds. In these experiments, efficacy was reached at 20-30 volts (about 66 and 100 V/cm) and toxicity was noticed when the current≥200 V/cm. These parameters are lower than those described for ciliary muscle [24] or squeletal muscle cells [16, 30]. Using selected parameters, electrotransfer was safe on fluorescein angiography, electroretinography and histology, demonstrating that it could be used even at the posterior pole without safety concerns. This is of course of the utmost importance if the macula should be targeted.

In these experiments, we did not use a specific gene promoter, but rather the CMV promoter, known to induce a short term transfection in RPE cells. Ongoing experiments are evaluating the efficacy of specific promoter to prolong the duration of expression as published by others [22, 23].

As compared to the recently developed suprachoroidal injection of viral vectors, the use of plasmid DNA and electroporation is expected to be safer since naked plasmid DNA do not have the ability to transfect cells, even if release in the systemic circulation, as already demonstrated in clinical trials using plasmid DNA electrotransfer in squeletal muscles [31].

Suprachorodal electroporation of plasmids could be used to target retinal cells as well as choroidal cells to produce anti-angiogenic proteins or peptides in situ for the treatment of choroidal neovascularization. As a proof of concept, we have used sFlt-1 that efficiently inhibited CNV not only in the treated temporal retina but also in the nasal untreated retina, demonstrating that local diffusion could occur. Other experiments are ongoing to evaluate the real potential of this novel method for the treatment of choroidal and retinal diseases.

Conclusion

This is the first demonstration that a safe procedure can be used to transfect not only the choroid, with potential applications for choroidal neovessels targeting, but also RPE cells and potentially photoreceptors. Not only non-viral vectors were used, but a minimally invasive procedure was performed avoiding retinal detachment and any intraocular electrode placement. Further technical improvements are ongoing to design a simple disposable device to treat specifically the posterior pole of human size eyes.

REFERENCES

Throughout this application, various references describe the state of the art to which this invention pertains. The disclosures of these references are hereby incorporated by reference into the present disclosure.

1. Hamel C (2006). Retinitis pigmentosa. Orphanet J Rare Dis; 1: 40.
2. Acland G M, Aguirre G D, Ray J, Zhang Q, Aleman T S, Cideciyan A V, et al. (2001). Gene therapy restores vision in a canine model of childhood blindness. Nat Genet; 28: 92-95.
3. Acland G M, Aguirre G D, Bennett J, Aleman T S, Cideciyan A V, Bennicelli J, et al. (2005). Long-term restoration of rod and cone vision by single dose rAAV-mediated gene transfer to the retina in a canine model of childhood blindness. Mol Ther; 12: 1072-1082.
4. Bainbridge J W, Smith A J, Barker S S, Robbie S, Henderson R, Balaggan K, et al. (2008). Effect of gene therapy on visual function in Leber's congenital amaurosis. N Engl J Med; 358: 2231-2239.
5. Hauswirth W W, Aleman T S, Kaushal S, Cideciyan A V, Schwartz S B, Wang L, et al. (2008). Treatment of leber congenital amaurosis due to RPE65 mutations by ocular subretinal injection of adeno-associated virus gene vector: short-term results of a phase I trial. Hum Gene Ther; 19: 979-990.
6. Maguire A M, Simonelli F, Pierce E A, Pugh E N, Jr., Mingozzi F, Bennicelli J, et al. (2008). Safety and efficacy of gene transfer for Leber's congenital amaurosis. N Engl J Med; 358: 2240-2248.
7. Romano G (2009). An update on gene therapy programs. Drug News Perspect; 22: 435-440.
8. Provost N, Le Meur G, Weber M, Mendes-Madeira A, Podevin G, Cherel Y, et al. (2005). Biodistribution of rAAV vectors following intraocular administration: evidence for the presence and persistence of vector DNA in the optic nerve and in the brain. Mol Ther; 11: 275-283.
9. Stieger K, Schroeder J, Provost N, Mendes-Madeira A, Belbellaa B, Le Meur G, et al. (2009). Detection of intact rAAV particles up to 6 years after successful gene transfer in the retina of dogs and primates. Mol Ther; 17: 516-523.
10. Le Meur G, Stieger K, Smith A J, Weber M, Deschamps J Y, Nivard D, et al. (2007). Restoration of vision in RPE65-deficient Briard dogs using an AAV serotype 4 vector that specifically targets the retinal pigmented epithelium. Gene Ther; 14: 292-303.
11. Wakabayashi T, Oshima Y, Fujimoto H, Murakami Y, Sakaguchi H, Kusaka S, et al. (2009). Foveal microstructure and visual acuity after retinal detachment repair: imaging analysis by Fourier-domain optical coherence tomography. Ophthalmology; 116: 519-528.
12. Wilkinson C P (2009). Mysteries regarding the surgically reattached retina. Trans Am Ophthalmol Soc; 107: 55-57.
13. Andrieu-Soler C, Bejjani R A, de Bizemont T, Normand N, BenEzra D, Behar-Cohen F (2006). Ocular gene therapy: a review of nonviral strategies. Mol Vis; 12: 1334-1347.
14. Bejjani R A, Andrieu C, Bloquel C, Berdugo M, BenEzra D, Behar-Cohen F (2007). Electrically assisted ocular gene therapy. Sury Ophthalmol; 52: 196-208.
15. Bloquel C, Bourges J L, Touchard E, Berdugo M, BenEzra D, Behar-Cohen F (2006). Non-viral ocular gene therapy: potential ocular therapeutic avenues. Adv Drug Deliv Rev; 58: 1224-1242.
16. Mir L M, Moller P H, Andre F, Gehl J (2005). Electric pulse-mediated gene delivery to various animal tissues. Adv Genet; 54: 83-114.
17. Mir L M (2008). Application of electroporation gene therapy: past, current, and future. Methods Mol Biol; 423: 3-17.
18. Isaka Y, Imai E (2007). Electroporation-mediated gene therapy. Expert Opin Drug Deliv; 4: 561-571.

19. Daud A I, DeConti R C, Andrews S, Urbas P, Riker A I, Sondak V K, et al. (2008). Phase I trial of interleukin-12 plasmid electroporation in patients with metastatic melanoma. J Clin Oncol; 26: 5896-5903.

20. Matsuda T, Cepko C L (2004). Electroporation and RNA interference in the rodent retina in vivo and in vitro. Proc Natl Acad Sci USA; 101: 16-22.

21. Chen B, Cepko C L (2009). HDAC4 regulates neuronal survival in normal and diseased retinas. Science; 323: 256-259.

22. Johnson C J, Berglin L, Chrenek M A, Redmond T M, Boatright J H, Nickerson J M (2008). Technical brief: subretinal injection and electroporation into adult mouse eyes. Mol Vis; 14: 2211-2226.

23. Kachi S, Oshima Y, Esumi N, Kachi M, Rogers B, Zack D J, et al. (2005). Nonviral ocular gene transfer. Gene Ther; 12: 843-851.

24. Touchard E, Kowalczuk L, Bloquel C, Naud M C, Bigey P, Behar-Cohen F (2010). The ciliary smooth muscle electrotransfer: basic principles and potential for sustained intraocular production of therapeutic proteins. J Gene Med; 12: 904-919.

25. Einmahl S, Behar-Cohen F, D'Hermies F, Rudaz S, Tabatabay C, Renard G, et al. (2001). A new poly(ortho ester)-based drug delivery system as an adjunct treatment in filtering surgery. Invest Ophthalmol Vis Sci; 42: 695-700.

26. Olsen T W, Feng X, Wabner K, Conston S R, Sierra D H, Folden D V, et al. (2006). Cannulation of the suprachoroidal space: a novel drug delivery methodology to the posterior segment. Am J Ophthalmol; 142: 777-787.

27. Hussain A A, Starita C, Hodgetts A, Marshall J (2010). Macromolecular diffusion characteristics of ageing human Bruch's membrane: implications for age-related macular degeneration (AMD). Exp Eye Res; 90: 703-710.

28. Wang L, Li C M, Rudolf M, Belyaeva O V, Chung B H, Messinger J D, et al. (2009). Lipoprotein particles of intraocular origin in human Bruch membrane: an unusual lipid profile. Invest Ophthalmol Vis Sci; 50: 870-877.

29. Peden M C, Min J, Meyers C, Lukowski Z, Li Q, Boye S L, et al. (2011) Ab-Externo AAV-Mediated Gene Delivery to the Suprachoroidal Space Using a 250 Micron Flexible Microcatheter. PLoS One; 6: e17140.

30. Aihara H, Miyazaki J (1998). Gene transfer into muscle by electroporation in vivo. Nat Biotechnol; 16: 867-870.

31. Low L, Mander A, McCann K, Dearnaley D, Tjelle T, Mathiesen I, et al. (2009). DNA vaccination with electroporation induces increased antibody responses in patients with prostate cancer. Hum Gene Ther; 20: 1269-1278.

32. Paques M, Simonutti M, Roux M J, Picaud S, Levavasseur E, Bellman C, et al. (2006) High resolution fundus imaging by confocal scanning laser ophthalmoscopy in the mouse. Vision Res; 46: 1336-1345.

33. Touchard E, Bloquel C, Bigey P, Kowalczuc L, Jonet L, Thillaye-Goldenberg B, et al. (2009) Effects of ciliary muscle plasmid electrotransfer of TNF-alpha soluble receptor variants in experimental uveitis. Gene Ther; 16: 862-873.

The invention claimed is:

1. A method for treating an ocular disease in a subject comprising the steps of
  i) delivering a pharmaceutical composition formulated with a therapeutic nucleic acid of interest into the suprachoroidal space of the diseased eye and
  ii) exposing the region where the pharmaceutical composition was delivered to an electrical field, wherein a field intensity of the electrical field is superior or equal to 15 volts and is inferior to 60 volts.

2. The method of claim 1 wherein the nucleic acid of interest is inserted into a plasmid.

3. The method according to claim 1 wherein the nucleic acid of interest encodes for enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, a peptide which is an agonist or antagonist of a receptor or of an adhesion protein, antigens, antibodies, fragments or derivatives thereof and other essential constituents of the cell, proteins involved in the visual cycle within RPE cells, or structure proteins of retinal cells.

4. The method according to claim 1, wherein said ocular disease is a retinal disease.

5. The method according to claim 1, wherein said ocular disease is selected from the group consisting of ocular proliferative diseases, ocular neurodegenerative diseases, glaucoma, ocular infectious diseases, ocular inflammatory diseases such as conjunctivitis, keratitis, endothelitis, uveitis, choroiditis, retinitis, retinochoroiditis, anterior uveitis, and inflammatory optic neuropathies, retinal degenerations, retinitis pigmentosa, peripheral retinal degeneration, macular degeneration, dry age-related macular degeneration, ischemic retinopathy, retinal vascular diseases, ocular ischemia syndrome and other vascular anomalies, choroidal disorders and tumors, vitreous disorders, glial proliferation.

6. The method according to claim 1, wherein the nucleic acid encodes a soluble fragment of a therapeutic protein selected from the group consisting of: a TNF [alpha] receptor; a TGF [beta]2 receptor of VEGFR-1, VEGFR-2, VEGFR-3, CCR2 or MIP1; an antibody or an antibody fragment having recognition capacities for the purposes of immunotherapy, or a precursor of any one of these.

7. The method according to claim 1, wherein the pharmaceutical composition comprises viscosity building agents selected from the group consisting of polyvinyl alcohol, polyvinyl pyrrolidone, methyl cellulose, hydroxypropyl methylcellulose, hydroxyethyl cellulose, carboxymethyl cellulose, hydroxypropyl cellulose.

8. The method according to claim 1, wherein the electric field is performed by electroporation.

9. The method according to claim 1, wherein a total duration of application of the electric field is between 0.01 millisecond and 1 second.

10. The method according to claim 1, wherein the electrical field is applied by using two electrodes, one of said electrodes being introduced into the suprachoroidal space and the other one being applied on the surface of the eye at the opposing side where the suprachoroidal injection was performed.

11. The method according to claim 1, wherein the electrical field is applied by using two electrodes, one of said electrodes being applied on a surface of the sclera adjacent to the region where the suprachoroidal injection was performed and the other one being applied on a surface of the eye at the opposing side where the suprachoroidal injection was performed.

12. The method according to claim 1, wherein the ocular disease is intraocular neovessels or macular oedema and the method comprises delivering to the suprachoroidal space of a subject suffering therefrom a pharmaceutical composition formulated with a therapeutic nucleic acid encoding an anti VEGF, an anti VEGF receptor or an anti PLGF.

13. The method according to claim 1, wherein the ocular disease is retinitis pigmentosa and the method comprises delivering to the suprachoroidal space of a subject suffering therefrom a pharmaceutical composition formulated with a therapeutic nucleic acid encoding a neurotrophic factor.

14. The method according to claim 1, wherein the ocular disease is diabetic retinopathy and the method comprises delivering to the suprachoroidal space of a subject suffering therefrom a pharmaceutical composition formulated with a therapeutic nucleic acid encoding an anti IRS-1 or IGF-1.

15. The method of claim 3, wherein said receptors are soluble receptors.

16. The method of claim 5, wherein said ischemic retinopathy is retinopathy of prematurity or diabetic retinopathy.

17. The method of claim 5, wherein said glial proliferation is proliferative vitreo retinopathy or glial proliferation associated with diabetic pre retinal angiogenesis.

18. The method of claim 6, wherein said antibody fragment is a variable fragment of a single-chain antibody (ScFv).

19. The method of claim 9, wherein the total duration of application of the electric field is selected from the group consisting of: between 0.01 and 500 milliseconds, between 1 and 500 milliseconds, between 10 milliseconds and 100 milliseconds, and 20 milliseconds.

20. The method of claim 11, wherein the surface of the eye at the opposing side is sclera or conjunctiva.

* * * * *